(12) United States Patent
Tanaka et al.

(10) Patent No.: US 8,785,662 B2
(45) Date of Patent: Jul. 22, 2014

(54) ANILIDE-BASED COMPOUNDS FOR PRESERVING WOOD AND METHOD OF USE THEREOF

(75) Inventors: Keijitsu Tanaka, Ibaraki (JP); Masahiro Maesawa, Tokyo (JP)

(73) Assignee: SDS Biotech K.K., Tokyo (JP)

( * ) Notice: Subject to any disclaimer, the term of this patent is extended or adjusted under 35 U.S.C. 154(b) by 0 days.

(21) Appl. No.: 13/696,677

(22) PCT Filed: May 12, 2010

(86) PCT No.: PCT/JP2010/058031
§ 371 (c)(1),
(2), (4) Date: Nov. 7, 2012

(87) PCT Pub. No.: WO2011/142009
PCT Pub. Date: Nov. 17, 2011

(65) Prior Publication Data
US 2013/0059014 A1    Mar. 7, 2013

(51) Int. Cl.
*A01N 43/08*        (2006.01)

(52) U.S. Cl.
CPC ................................. *A01N 43/08* (2013.01)
USPC ............ 549/200; 424/638; 514/471; 514/383

(58) Field of Classification Search
CPC ............................. A01N 43/08; C07D 307/42
USPC .......................................... 424/638; 549/487
See application file for complete search history.

(56) References Cited

U.S. PATENT DOCUMENTS

| | | | |
|---|---|---|---|
| 3,959,481 A | 5/1976 | Davis et al. | |
| 4,093,743 A | 6/1978 | Yabutani et al. | |
| 4,123,554 A | 10/1978 | Kawada et al. | |
| 4,942,178 A * | 7/1990 | Toyoda et al. | 514/617 |
| 5,977,168 A | 11/1999 | Konishi et al. | |
| 6,506,913 B2 * | 1/2003 | Konishi et al. | 549/487 |
| 2009/0293761 A1 * | 12/2009 | Richardson et al. | 106/18 |

FOREIGN PATENT DOCUMENTS

| | | |
|---|---|---|
| GB | 1 215 066 A | 12/1970 |
| GB | 1 217 868 A | 12/1970 |
| JP | 53-9739 A | 1/1978 |
| JP | 53-12973 B | 2/1978 |
| JP | 55-41202 B1 | 10/1980 |
| JP | 60-197603 A | 10/1985 |
| JP | 62-249975 A | 10/1987 |
| JP | 63-38966 B2 | 8/1988 |
| JP | 1-143804 A | 6/1989 |
| JP | 6-220035 A | 8/1994 |
| JP | 2825745 B2 | 11/1998 |
| JP | 2951772 B2 | 9/1999 |
| JP | 3083659 B2 | 9/2000 |
| JP | 2009-96751 A | 5/2009 |
| JP | 2010-150186 A | 8/2010 |

OTHER PUBLICATIONS

Hagmann; Title: The many roles for fluorine in medicinal chemistry; Journal of Medicinal Chemistry, vol. 51(15), pp. 4359-4369, published Aug. 14, 2008).*

* cited by examiner

*Primary Examiner* — Richard Schnizer
*Assistant Examiner* — Yanzhi Zhang
(74) *Attorney, Agent, or Firm* — Sughrue Mion, PLLC

(57) ABSTRACT

The present invention relates to a preservative for preserving wood comprising 5-methyl-2-trifluoromethylfuran-3-carboxylic acid anilide derivative represented by the following formula,

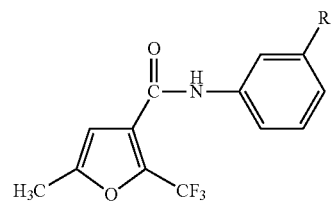

wherein R represents an iropropyl group or an isopropoxy group as an active ingredient. The preservative for preserving wood has an excellent preservative effect on various wood-decay fungi at an extremely low dose, is economically efficient, and imposes a small burden on the environment. The present invention also relates to a method for treating wood using the preservative.

7 Claims, No Drawings

US 8,785,662 B2

ANILIDE-BASED COMPOUNDS FOR PRESERVING WOOD AND METHOD OF USE THEREOF

CROSS REFERENCE TO RELATED APPLICATIONS

This application is a National Stage of International Application No. PCT/JP2010/058031, filed on May 12, 2010, the contents of all of which are incorporated herein by reference in their entirety.

TECHNICAL FIELD

The present invention relates to a wood preservative. Specifically, the present invention relates to a wood preservative containing 3'-isopropyl-5-methyl-2-trifluoromethylfuran-3-carboxylic acid anilide and/or 3'-isopropoxy-5-methyl-2-trifluoromethylfuran-3-carboxylic acid anilide having an antifungal effect against wood decay fungi, which enables a small environmental load as well as improved economic efficiency owing to its excellent antifungal effect against wood decay fungi, and a wood preservative further containing a triazole compound in addition to 3'-isopropyl-5-methyl-2-trifluoromethylfuran-3-carboxylic acid anilide and/or 3'-isopropoxy-5-methyl-2-trifluoromethylfuran-3-carboxylic acid anilide, which enables reducing an environmental load as well as further improving the antifungal effect against wood decay fungi and economic efficiency by the synergetic effect.

BACKGROUND ART

Although the wood is a useful material widely used in various fields, it has a disadvantage of being decayed by wood-destroying fungi and degrading, which causes significant deterioration in the strength. Hence, various inorganic and organic preservative agents have been conventionally used in order to prevent deterioration by various wood-destroying fungi. However, it has been pointed out that such agents have a problem of imposing a huge impact on the human body and a great burden on the environment when they are used in high concentration. Hence, there is a great demand for a more effective preservative agent, which is economical and has a small environmental load.

3'-isopropyl-5-methyl-2-trifluoromethylfuran-3-carboxylic acid anilide (may be hereinafter referred to as "compound A" for short) and 3'-isopropoxy-5-methyl-2-trifluoromethylfuran-3-carboxylic acid anilide (may be hereinafter referred to as "compound B" for short) used as an active ingredient in the present invention belongs to the carboxamide fungicide. There are a number of documents relating to the carboxamide fungicide since old times. For example JP-A-S53-9739 (Patent Document 1) (U.S. Pat. No. 4,093,743) proposes o-trifluoromethyl-m'-isopropoxy benzoic acid anilide to control rice sheath blight, JP-B-S53-12973 (Patent Document 2) (U.S. Pat. No. 4,123,554) proposes 2-methyl benzanilide derivative as a bactericide for agricultural and horticultural use, JP-B-S55-41202 (Patent Document 3) proposes benzamide derivative having a specific structure as an agricultural and horticultural fungicide, JP-A-S60-197603 (Patent Document 4) proposes o-trifluoromethyl-m'-isopropoxy benzoic acid anilide as a Serpula lacrymans control agent, JP-B-S63-38966 (Patent Document 5) proposes a compound of 2-substituted benzanilide compound having a specific structure as a wood preservative and antifungal agent, JP-A-H01-143804 (Patent Document 6) (U.S. Pat. No. 4,942,178) discloses 3'-isopropyl benzanilide derivative having a specific structure as a fungicide for agricultural and horticultural use, JP-B-S48-1171 (Patent Document 7) proposes an acid anilide derivative having a specific structure as a composition for a fungicide, JP-B-S50-10376 (Patent Document 8) (U.S. Pat. No. 3,959,481) proposes a furan-3-carboxyamide derivative having a specific structure as a composition to protect plants from diseases, Japanese Patent 2825745 (Patent Document 9) (U.S. Pat. No. 5,977,168) proposes a dimethylfurancarboxyanilide derivative having a specific structure as a wood preservative and Japanese Patent No. 2951772 (Patent Document 10) and Japanese Patent No. 3083659 (Patent Document 11) disclose 2,5-dimethylfuran-3-carboxyanilide as a wood preservative composition or a wood preservative. However, these publications neither disclose compound A or B of the present invention nor mention a synthesis example, activity to wood-destroying fungi or the like of the compounds.

PRIOR ART DOCUMENTS

Patent Documents

Patent Document 1: JP-A-S53-9739
Patent Document 2: JP-B-S53-12973
Patent Document 3: JP-B-S55-41202
Patent Document 4: JP-A-S60-197603
Patent Document 5: JP-B-S63-38966
Patent Document 6: JP-A-H01-143804
Patent Document 7: JP-B-S48-1171
Patent Document 8: JP-B-S50-10376
Patent Document 9: Japanese Patent No. 2825745
Patent Document 10: Japanese Patent No. 2951772
Patent Document 11: Japanese Patent No. 3083659

DISCLOSURE OF THE INVENTION

Problems to be Solved by the Invention

An objective of the present invention is to provide a wood preservative and a wood treatment method, which is more effective and economical with a small environmental load.

Means to Solve the Problem

The present inventors conducted intensive studies extensively regarding effective preservative ingredients against various wood-destroying fungi. As a result, they have found that excellent preservation effect with a very small chemical dosage can be obtained by containing compound A and/or B as an active ingredient. Furthermore, they have found that, when compound A and/or B and a triazole-based fungicide are contained as active ingredients, synergetic effect between the effects of the two ingredients is seen and excellent preservation effect can be attained with a even smaller chemical dosage. They have accomplished the present invention based on this finding.

That is, the present invention is to provide a wood preservative and a wood treating method as follows.

(1) A 5-methyl-2-trifluoromethylfuran-3-carboxyanilide derivative represented by the following formula [1]:

[Chem. 1]

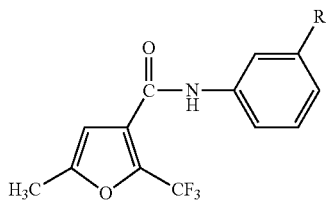

(In the formula, R represents an isopropyl group or an isopropoxy group).

(2) A wood preservative containing 3'-isopropyl-5-methyl-2-trifluoromethylfuran-3-carboxylic acid anilide and/or 3'-isopropoxy-5-methyl-2-trifluoromethylfuran-3-carboxylic acid anilide as described in (1) above as an active ingredient.

(3) The wood preservative as described in (2) above, which further contains a triazole-based fungicide.

(4) The wood preservative as described in (3) above, wherein the triazole-based fungicide is one or more members selected from cyproconazole, epoxyconazole and tetraconazole.

(5) The wood preservative as described in any one of (2) to (4) above, further containing other antibiotic compounds.

(6) The wood preservative as described in (5) above, wherein the antibiotic compound is selected from copper compounds.

(7) A wood preservative treatment method using the preservative as described in any one of (1) to (6) above.

Effects of the Invention

The present invention provides a 5-methyl-2-trifluoromethylfuran-3-carboxylic acid anilide derivative which is useful as a wood preservative; and a wood preservative and a wood treating method using the derivative.

The wood preservative of the present invention has excellent preservation effect against various wood-destroying fungi with a very small chemical dosage, is economical and has a small environmental load.

MODE FOR CARRYING OUT THE INVENTION 5-methyl-2-trifluoromethylfuran-3-carboxylic acid anilide derivative of the present invention is 3'-isopropyl-5-methyl-2-trifluoromethylfuran-3-carboxylic acid anilide (compound A) and 3'-isopropoxy-5-methyl-2-trifluoromethylfuran-3-carboxylic acid anilide (compound B). Compounds A and B can be produced by known methods and suitably produced by the method described as in the below reaction formula.

[Chem. 2]

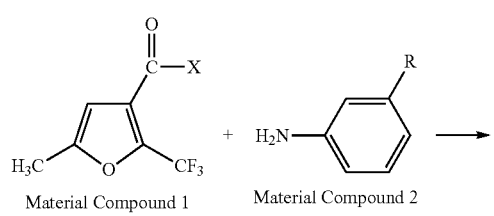

Material Compound 1    Material Compound 2

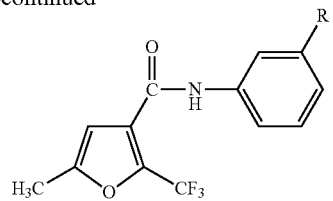

Compound A or B

In the above reaction formula, X represents a halogen atom such as chlorine, bromine and iodine, and X is preferably a chlorine atom. R represents an isopropyl group or an isopropoxy group. The material compound 1 can be obtained by halogenating known 5-methyl-2-trifluoromethylfuran-3-carboxylic acid, which is produced by known methods, using thionyl chloride, oxalyl chloride and the like. As the material compound 2, known 3-isopropyl aniline or 3-isopropoxy aniline produced by known methods can be used.

Compound A or B can be obtained by reacting the material compound 1 and material compound 2 in an inert solvent in the presence of dehydrohalogenation agent according to the above reaction formula.

Examples of the inert solvent include halogenated hydrocarbons such as dichloromethane, chloroform, dichloroethane and carbon tetrachloride; aromatic hydrocarbons such as benzene, toluene and xylene; ethers such as diethyl ether, isopropyl ether, tetrahydrofuran and dioxane; acetone; ethyl acetate; hexane; or a mixed solvent thereof.

As an example of the dehydrohalogenation agent, triethyl amine, diisopropyl ethyl amine, pyridine and the like may be used.

As the reaction temperature, a temperature within the range from 0° C. to the boiling point of the solvent may be selected, and preferably a temperature from room temperature to 150° C. may be selected.

There is no particular limitation on the reaction time and preferably it is about 0.5 to three hours.

The wood preservative of the present invention contains the above-mentioned 5-methyl-2-trifluoromethylfuran-3-carboxyanilide derivative as an active ingredient. In the wood preservative of the present invention, a triazole-based fungicide may further be combined as an active ingredient.

As a triazole-based fungicide used in combination in the present invention, a commercially available product can be used. Examples of the triazole-based fungicide include azaconazole, bitertanol, bromuconazole, cyproconazole, diniconazole, epoxiconazole, fenbuconazole, fluquinconazole, flusilazole, flutriafol, hexaconazole, imibenconazole, ipconazole, metconazole, myclobutanil, paclobutrazol, penconazole, propiconazole, tebuconazole, tetraconazole, triadimefon, triadimenol, triticonazole and uniconazole. Among these, preferred are cyproconazole, epoxiconazole and tetraconazole.

When the wood preservative of the present invention is actually used, the preservative may be used as produced without adding any other ingredients. However, generally, the preservative is applied after being mixed with solid carriers, liquid carriers or gas carriers with addition of a surfactant and other adjuvants for drug formulations as needed to thereby be formulated into the forms such as an oil solution, an emulsion, a solubilizer, a wettable powder, a suspension, a flowable formulation and a dust formulation.

Examples of the solvent which can be used for preparing these formulations include aromatic organic solvents such as toluene-based, xylene-based or methylnaphthalene-based solvents; halogenated hydrocarbon such as dichloromethane and trichloroethane; alcohols such as isopropyl alcohol and benzyl alcohol; glycol-based solvents such as polyethylene glycol and polypropylene glycol; kerosene; N-methylpyrolidone; ester phosphate; and benzoic acid ester.

As the surfactant to be used for formulations, an anionic, nonionic, cationic or zwitterionic surfactant can be used.

These formulations generally contain active ingredients (compound A and/or compound B, or total amount of compound A and/or compound B and a triazole-based fungicide) in an amount of 0.01 to 90 mass %, and preferably 0.1 to 50 mass %. When compound A and/or compound B and a triazole-based fungicide are used in mixture, the mixing ratio between compound A and/or compound B and the triazole-based fungicide is generally from 1:100 to 100:1, and preferably from 1:10 to 10:1.

When the wood preservative of the present invention is applied to the wood, the preservative concentration is generally from 0.1 to 500 g/m$^3$, and preferably from 1 to 100 g/m$^3$.

Using the wood preservative of the present invention in combination with other antibiotic compounds enables further enhancing the antibiotic effect and expanding the action spectrum of the drug. The wood treatment using these antibiotic compounds may be carried out as pretreatment or posttreatment of the preservative treatment by the present invention. However, it is effective in saving labor to formulate the antibiotic compound added to the wood preservative of the present invention to thereby carry out the wood treatment at the same time.

Preferable examples of the antibiotic compound which can be used for the above-mentioned purpose include copper compounds. Examples of the copper compound include copper sulfate, copper chloride, copper phosphate, copper hydroxide, copper carbonate, basic copper carbonate, basic copper acetate, basic copper phosphate, basic copper chloride, copper oxide, copper(I) oxide, copper acetate, copper naphthenate, copper oleate, copper stearate, copper octanoate, copper benzoate, copper citrate, copper lactate, copper tartrate, copper 2-ethylhexanoate, complexes of these compounds stabilized as a water-soluble component; and hydrates of these compounds.

When the formulation containing the above-mentioned copper compounds is designed as the wood preservative of the present invention, the blend ratio between the copper compound and compound A and/or B is generally 10:1 to 1000:1, and preferably from 20:1 to 500:1 by mass. In the case where these formulations are designed to be water-reducible, a copper compound is generally brought into a stable solution and conventionally known ammonium compounds and amine compounds can be used. Specific example of the compounds include ammonia, ammonium carbonate, ammonium bicarbonate, ethanolamine, diethanolamine, triethanolamine, propanolamine, triisopropanolamine, N-methylethanolamine, N-methyl diethanolamine, N,N-dimethylethanolamine, N-ethylethanolamine, N-ethyldiethanolamine, isopropanol amine, aminoethylethanolamine, ethylenediamine, diethylenetriamine, triethylenetetramine, tetraethylenepentamine, pentaethylenehexamine, polyethyleneimine, N,N-dimethylethylenediamine, 1,2-propanediamine, 1,3-propanediamine and polyallylamine. Also, various carbonate compounds, carboxylic compounds or mineral acids may be further added to control the pH. Specifically, boric acid, naphthenic acid, formic acid, acetic acid, propionic acid, hexanoic acid, heptanoic acid, octanoic acid, stearic acid, palmitic acid, oleic acid, benzoic acid, citric acid, lactic acid, tartaric acid, malic acid, succinic acid, adipic acid, fumaric acid, malonic acid, gulconic acid, sebacic acid, cyclohexanoic acid, 2-ethylhexanoic acid, isooctanoic acid, sodium bicarbonate, ammonium bicarbonate, phosphoric acid, sodium dihydrogen phosphate, potassium dihydrogen phosphate and hydrates thereof may be used.

In the wood preservative of the present invention, preferred examples of the other antibiotic compounds to be used in combination for the purpose of enhancing the antibiotic effect and expanding the action spectrum include strobins such as azoxystrobin, picoxystrobin and pyraclostrobin; sulfonamides such as dichlorofluanid (Euparene), tolyfluanid (Methyleuparene), cyclofluanid, folpet and fluorofolpet; benzimidazoles such as carbendazim (MBC), benomyl, fuberitazole, thiabendazole and salts thereof; thiocyanates such as thiocyanatemethylthio benzothiazole (TCMTB), and methylene bis thiocyanate (MBT); quaternary ammonium salts such as benzyl dimethyl tetradecyl ammonium chloride, benzyl-dimethyl-dodecyl ammonium chloride, didecyl-dimethyl ammonium chloride and N-alkyl benzyl methyl ammonium chloride; morpholine derivatives such as 4-($C_{11}$ to $C_{14}$ alkyl)-2,6-dimethylmorpholine homologues (Tridemorph) and (±)-cis-4-[3-(t-butylphenyl)-2-methylpropyl]-2,6-dimethylmorpholine (Fenpropimorph, Falimorph); phenols such as o-phenylphenol, tribromophenol, tetrachlorophenol, pentachlorophenol, 3-methyl-4-chlorophenol, dichlorophenol, chlorophen and salts thereof; organic iodine compounds such as 3-iodo-2-propynyl-n-butyl carbamate (IPBC), 3-iodo-2-propynyl-n-hexyl carbamate, 3-iodo-2-propynyl cyclohexyl carbamate, 3-iodo-2-propynyl phenyl carbamate, 3-iodo-2-propynil-n-butyl carbamate, p-chlorophenyl-3-iodo propargylformal (IF-1000), 3-bromo-2,3-diiodo-2-propenylethyl carbonate (Sunplus) and 1-[(diiodomethyl)sulfonyl]-4-methylbenzene (Amical); organic bromo derivatives such as Bronopol; benzisothiazolines such as N-methylisothiazoline-3-on, 5-chloro-N-methylisothiazoline-3-on, 4,5-dichloro-N-octylisothiazoline-3-on and N-octylisothiazoline-3-on (Octylinone); benzisothiazolines such as cyclopentaisothiazoline; pyridines such as 1-hydroxy-2-pyridinethione (or sodium salts, iron salts, manganese salts, zinc salts and the like thereof) and tetrachloro-4-methylsulfonylpyridine; metal soaps such as naphthate, octoate, 2-ethylhexanoate, oleate, phosphate, benzoate and the like of tin, copper and zinc; oxides such as $Cu_2O$, CuO and ZnO; organic tin derivatives such as tributyltin naphthenate and t-butyltin oxide; metal compounds such as tris-N-(cyclohexyldiazenium dioxine)tributyl tin or potassium salts, and bis-(N-cyclohexyl) diazonium-dioxine copper or aluminum; carbamates such as sodium or zinc salts of dialkyl dithiocarbamate and tetramethylthiuram disulfide (TMTD); nitriles such as 2,4,5,6-tetrachloroisophthalonitrile (Chlorothalonil); antimicrobial agents having an activated halogen atom such as tectamer, bronopol and brumidox; benzothiazoles such as 2-mercaptobenzothiazole and dazomet; quinolines such as 8-hydroxyquinoline; compounds generating formaldehyde such as benzylalcoholmono(poly)hemiformal, oxazolidine, hexahydro-s-triazine and N-methylol-chloroacetamide; boron compounds such as disodium octaborate tetrahydrate, boric acid and borax; fluorine compounds such as sodium fluoride and sodium fluorosilicate; ester phosphates such as azinphosethyl, azinphos-methyl, 1-(4-chlorophenyl)-4-(O-ethyl, S-propyl)phosphoryloxypyrazole (TIA-230), chlorpyriphos, tetrachlorvinphos, coumaphos, dethomen-5-methyl, diazinon, dichlorvos, dimethoate, ethoprophos, etholimphos, fenitrothion, pyridafenthion, heptenophos, parathion, parathion-methyl, propetanphos, phosalone, phoxim, pyrimphos-ethyl, pyrimiphos-methyl, profenophos, prothiophos, sulprophos, triazophos and trichlorfon; carbamates such as aldicarb, beniocarb, BPMC (2-(1-methylpropyl)phenylmethyl carbamate), butocarboxym, butoxycarboxym, carbaryl, carbofuran, carbosulfan, chloethocarb, isoprocarb, methomyl, oxamyl, pirimicarb, promecarb, propoxur and thiodicarb; pyrethroids such as allethrin, alphamethrin, empenthrin, profluthrin, tralomethrin, methofluthrin, phenothrin, imiprothrin, cyphenothrin, futarthrin, pyrethrin, prallethrin, furamethrin, dimefluthrin, profluthrin, tefluthrin, bioallethrin, esbiothrin, bioresmethrin, cycloprothrin, cyfluthrin, decamethrin, cyhalothrin, cypermethrin, deltamethrin, permethrin, resmethrin, fenpropathrin, fenfluthrin, fenvalerate, flucythrinate, flumthrin, fluvalinate and ethophenprox; neonicotinoids such as acetamiprid, imidacloprid, thiacloprid, chlothianidin, dinotefuran, thiamethoxam and nitenpyram.

Preferred examples of the antibiotic compound which can be used for the objective of the present invention also include quaternary ammonium compounds represented by the following formula.

$$[R^1R^2N^+R^3R^4]_nX^{n-}$$ [Chem. 3]

(In the formula, $R^1$, $R^2$, $R^3$ and $R^4$ represent an organic substituent having 20 or less carbon atoms which are joined by a carbon-nitrogen bond, $X^-$ represents an inorganic or organic anion having a valence of n, and n is 1, 2 or 3.) Specific examples include didecyl dimethyl ammonium chloride, benzalkonium chloride, dioctyl dimethyl ammonium chloride, dilauryl dimethyl ammonium chloride, lauryl trimethyl ammonium chloride, cetyl trimethyl ammonium chloride, octadecyl picolinium chloride, octyldecyl pyridinium ammonium chloride and lauryl isoquinolium bromide.

The wood treatment by these antibiotic compounds may be carried out as pretreatment or posttreatment of the wood treatment by the wood preservative of the present invention. However, as is the case for the above-mentioned copper compounds, it is effective in saving labor to formulate the antibiotic compound added to the wood preservative of the present invention to thereby carry out the wood treatment at the same time. When the formulation containing the above-mentioned antibiotic compounds is designed as the wood preservative of the present invention, the blend ratio between the antibiotic compound and compound A and/or B is generally 0.01:1 to 1000:1, and preferably from 0.1:1 to 500:1 by mass.

These antibiotic compounds may be used solely or in combination of the two or more thereof.

[Wood-Destroying Fungi]

The wood preservative of the present invention is effective on the wood-destroying fungi including the following kinds of fungi: basidiomycetes including *Coniophora puteana, Trametes versicolor, Postia placenta, Poria vaporaria, Poria vaillantii, Gloeophyllum sepiarium, Gloeophyllum odoratum, Gloeophyllum abietinum, Gloeophyllum trabeum, Gloeophyllum protactum, Lentinus lepideus, Lentinus edodes, Lentinus cyathiformes, Lentinus squarrolosus, Paxillus panuoides, Fomitopsis palustris, Pleurotus ostreatus, Donkioporia expansa, Serpula lacrymans, Serpula himantoides, Glenospora graphii, Fomitopsis lilacino-gilva, Perenniporia tephropora, Antrodia xantha* and *Antrodia vaillantii*; Deuteromycetes including *Cladosporium herbarum*; and Ascomycetes including *Chaetomium globosum, Chaetomium alba-arenulum, Petriella setifera, Trichurus spiralis* and *Humicola grisera*.

The wood preservative of the present invention is effective on the sap-staining fungi including the following kinds of fungi: Deuteromycetes including *Aureobasidium pullulans, Scleroph pithyophila, Scopular phycomyces, Aspergillus niger, Penicillium variabile, Trichoderma viride, Trichoderma rignorum* and *Dactyleum fusarioides*; Ascomycetes including *Caratocystis minor*; and Zygomycetes including *Mucor spinosus*.

Treatment Object:

The wood preservative of the present invention is available as the treatment agent of various wood materials, and exerts a positive effects in the treatment of the timber, wood chips, wood meal, plywood, laminated veneer lumber, fiberboard, particle board, manufactured wood products, chaffs, straws, bamboos and the like.

Application as the Wood Preservative:

The wood preservative of the present invention can be used for the treatment of the lumber, timber, manufactured wood product and wood building. For example, the preservative can be applied to any of the groundsill, sleeper, joist, floor board, furring strip, stud, sheathing floor board, brace, balk, sheathing roof board, bathroom framework and floor framing, exterior materials, log house, balcony, terrace, gate and fence, bower, open verandah, materials for outdoor buildings such as deck materials, railway sleeper, telephone pole, foundation pile, sound abatement shield and civil engineering construction such as bridges. The preservative can be applied to the wood of any form such as logs, boards, square timbers, bars, plywood, laminated veneer lumbers and chipboards.

The treatment using the wood preservative of the present invention can be carried out for the above-mentioned objects in the same way as the usual method carried out as the decay prevention measures. Generally, the application treatment, spraying treatment, dipping treatment, pressure treatment, drilling treatment and the like are performed as the wood treatment; and the treatment on the veneer, treatment by using an adhesive as a chemical mixture, treatment on the plywood laminate and the like are performed as the treatment on the plywood and the laminated veneer lumber. The preservative of the present invention can be applied to any of these treatments.

EXAMPLES

The invention will be described with reference to Examples below, but the invention is not limited to the description.

Preparation of the compound

Synthesis Example 1

Compound A 1.0 g of 5-methyl-2-trifluoromethylfuran-3-carbonyl chloride (manufactured by Namiki Shoji Co., Ltd.) was dissolved in 20 ml of methylene chloride, and 0.66 ml of triethylamine (manufactured by Wako Pure Chemical Industries, Ltd.) was added thereto while being cooled in ice. After adding 0.64 g of 3-isopropyl aniline (manufactured by Tokyo Chemical Industry Co., Ltd.), the mixture was stirred at room temperature for one hour and refluxed for one hour to cause reaction. After cooling the solution, 20 ml of methylene chloride was added thereto. After washing the solution with 40 ml of 1N NaOH, 40 ml of 1N HCl and 40 ml of saturated saline, the solution was dehydrated with $Na_2SO_4$ and condensed using an evaporator. The obtained reaction product was purified using silica gel column chromatography, and recrystallized using an ethyl acetate/hexane-based solvent to thereby obtain 1.1 g of colorless crystals of 3'-isopropyl-5-methyl-2-trifluoromethylfuran-3-carboxylic acid anilide.

The melting point: 103 to 105° C.

¹H-NMR (CDCl₃) δppm; 7.56-6.99 (5H, m), 6.40 (1H, s), 3.00-2.83 (1H, m), 2.36 (3H, s), 1.29 (3H, s), 1.21 (3H, s)

Synthesis Example 2

Compound B

The same reaction and posttreatment operation were performed as in Synthesis Example 1 using 0.9 g of 5-methyl-2-trifluoromethylfuran-3-carbonyl chloride, 0.56 ml of triethylamine and 0.6 g of 3-isopropoxyaniline (manufactured by Sigma-Aldrich Japan) to thereby obtain 1.0 g of pale yellow crystals of 3'-isopropoxy-5-methyl-2-trifluoromethylfuran-3-carboxylic acid anilide.
The melting point: 86 to 89° C.,
¹H-NMR (CDCl₃) δppm; 7.50-6.62 (5H, m), 6.40 (1H, s), 4.70-4.43 (1H, m), 2.37 (3H, s), 1.37 (3H, s), 1.30 (3H, s)

Synthesis Example 3

Comparative Compound 1 (Compound Disclosed by Japanese Patent No. 2825745 (U.S. Pat. No. 5,977,168))

The same reaction and posttreatment operation were performed as in Synthesis Example 1 using 1.0 g of 2,5-dimethylfuran-3-carbonyl chloride (manufactured by Sigma-Aldrich Japan), 0.88 ml of triethylamine and 0.85 g of 3-isopropylaniline to thereby obtain 1.2 g of pale yellow crystals of 3'-isopropyl-2,5-dimethylfuran-3-carboxylic acid anilide.
The melting point: 81 to 84° C.,
¹H-NMR (CDCl₃) δppm; 7.43-6.92 (5H, m), 6.09 (1H, s), 2.98-2.75 (1H, m), 2.58 (3H, s), 2.28 (3H, s), 1.29 (3H, s), 1.22 (3H, s), Synthesis Example 4

Comparative Compound 2 (Compound Disclosed by Japanese Patent No. 2825745 (U.S. Pat. No. 5,977,168))

The same reaction and posttreatment operation were performed as in Synthesis Example 1 using 1.0 g of 2,5-dimethylfuran-3-carbonyl chloride, 0.88 ml of triethylamine and 0.85 g of 3-ethylaniline to thereby obtain 1.1 g of white crystals of 3'-ethyl-2,5-dimethylfuran-3-carboxylic acid anilide.
The melting point: 113 to 115° C.
¹H-NMR (CDCl₃) δppm; 7.47-6.95 (4H, m), 6.09 (1H, s), 2.66 (3H, q), 2.58 (3H, s), 2.28 (3H, s), 1.25 (3H, t)

Synthesis Example 5

Comparative Compound 3 (Compound Disclosed by Japanese Patent No. 3083659)

The same reaction and posttreatment operation were performed as in Synthesis Example 1 using 1.0 g of 2,5-dimethylfuran-3-carbonyl chloride, 0.88 ml of triethylamine and 0.85 g of 3-methylaniline to thereby obtain 1.1 g of white crystals of 3'-methyl-2,5-dimethylfuran-3-carboxylic acid anilide.
The melting point: 100 to 102° C.,
¹H-NMR (CDCl₃) δppm; 7.48-6.09 (5H, m), 2.36 (3H, s), 2.60 (3H, s), 2.28 (3H, s)

Synthesis Example 6

Comparative Compound 4 (Compound Disclosed by JP-A-S53-9739 (U.S. Pat. No. 4,093,743), JP-A-S60-197603 and JP-B-S63-38966)

The same reaction and posttreatment operation were performed as in Synthesis Example 1 using 1.0 g of 2-trifluoromethyl benzoic acid chloride (manufactured by Sigma-Aldrich Japan), 0.70 ml of triethylamine and 0.76 g of 3-isopropoxyaniline to thereby obtain 1.4 g of pale yellow crystals of 3'-isopropoxy-2-trifluoromethyl benzoic acid anilide.
The melting point: 103 to 106° C.
¹H-NMR (CDCl₃) δppm; 7.88-6.64 (9H, m), 4.69-4.42 (1H, m), 1.37 (3H, s), 1.30 (3H, s)

Synthesis Example 7

Comparative Compound 5 (Compound Disclosed by JP-B-S63-38966)

The same reaction and posttreatment operation were performed as in Synthesis Example 1 using 0.77 g of 2-methylbenzoyl chloride (manufactured by Sigma Aldrich Japan), 0.70 ml of triethylamine and 0.76 g of 3-isopropoxyaniline to thereby obtain 1.3 g of colorless crystals of 3'-isopropoxy-2-methylbenzoic acid anilide.
The melting point: 87 to 90° C.
¹H-NMR (CDCl₃) δppm; 7.49-6.62 (9H, m), 4.69-4.43 (1H, m), 2.47 (3H, s), 1.36 (3H, s), 1.30 (3H, s)

Synthesis Example 8

Comparative Compound 6 (Compound Disclosed by JP-B-S53-12973 (U.S. Pat. No. 4,123,554))

The same reaction and posttreatment operation were performed as in Synthesis Example 1 using 1.0 g of 2-methylbenzoyl chloride (manufactured by Sigma-Aldrich Japan), 0.88 ml of triethylamine and 0.85 g of 3-isopropylaniline to thereby obtain 1.5 g of pale brown crystals of 3'-isopropyl-2-methylbenzoic acid anilide.
The melting point: 80 to 83° C.
¹H-NMR (CDCl₃) δppm; 7.53-6.92 (9H, m), 3.07-2.70 (1H, m), 2.51 (3H, s), 1.30 (3H, s), 1.23 (3H, s)

Synthesis Example 9

Comparative Compound 7

0.28 g of 3-furancarboxylic acid (manufactured by Sigma-Aldrich Japan) and 0.34 g of 3-isopropylaniline were dissolved in 20 ml of methylene chloride, and 0.53 g of WSCI/HCl (manufactured by Tokyo Chemical Industry Co., Ltd.) was added thereto while being cooled in ice. The mixture was stirred at room temperature for one hour, and refluxed for one hour to cause reaction. Then, the same reaction and posttreatment operation were performed as in Synthesis Example 1 to thereby obtain 0.34 g of pale yellow crystals of 3'-isopropyl-3-furancarboxylic acid anilide.
The melting point: 88 to 91° C.
¹H-NMR (CDCl₃) δppm; 8.01-6.70 (8H, m), 3.05-2.75 (1H, m), 1.25 (3H, s), 1.20 (3H, s)

Synthesis Example 10

Comparative Compound 8

0.32 g of 2-methyl-3-furancarboxylic acid (manufactured by Sigma-Aldrich Japan) and 0.34 g of 3-isopropylaniline were dissolved in 20 ml of methylene chloride, and 0.53 g of WSCI/HCl was added thereto while being cooled in ice. The mixture was stirred at room temperature for one hour, and refluxed for one hour to cause reaction. Then, the same reaction and posttreatment operation were performed as in Synthesis Example 1 to thereby obtain 0.34 g of pale yellow oily compound of 3'-isopropyl-2-methylfuran-3-carboxylic acid anilide.

$^1$H-NMR (CDCl$_3$) δppm; 7.43-6.52 (7H, m), 2.97-2.66 (1H, m), 2.63 (3H, s), 1.29 (3H, s), 1.21 (3H, s)

Synthesis Example 11

Comparative Compound 9

0.36 g of 4-methylthiazole-5-carboxylic acid (manufactured by Sigma-Aldrich Japan) and 0.34 g of 3-isopropylaniline were dissolved in 20 ml of methylene chloride, and 0.53 g of WSCI/HCl was added thereto while being cooled in ice. The mixture was stirred at room temperature for one hour, and refluxed for one hour to cause reaction. Then, the same reaction and posttreatment operation were performed as in Synthesis Example 1 to thereby obtain 0.40 g of colorless gum-like compound of 3'-isopropyl-4-methylthiazole-5-carboxylic acid anilide.

$^1$H-NMR (CDCl$_3$) δppm; 8.73 (1H, s), 7.54-6.98 (5H, m), 3.07-2.84 (1H, m), 2.79 (3H, s), 1.30 (3H, s), 1.22 (3H, s)

Synthesis Example 12

Comparative Compound 10

0.39 g of 2,4-dimethyl-1,3-thiazole-5-carboxylic acid (manufactured by Sigma-Aldrich Japan) and 0.34 g of 3-isopropylaniline were dissolved in 20 ml of methylene chloride, and 0.53 g of WSCI/HCl was added thereto while being cooled in ice. The mixture was stirred at room temperature for one hour, and refluxed for one hour to cause reaction. Then, the same reaction and posttreatment operation were performed as in Synthesis Example 1 to thereby obtain 0.45 g of pale yellow oily compound of 3'-isopropyl-2,4-dimethyl-1,3-thiazole-5-carboxylic acid anilide.

$^1$H-NMR (CDCl$_3$) δppm; 7.42-6.98 (5H, m), 2.99-2.75 (1H, m), 2.71 (6H, s), 1.29 (3H, s), 1.22 (3H, s)

Synthesis Example 13

Comparative Compound 11

0.46 g of 2-methyl-4-trifluoromethyl-1,3-thiazole-5-carboxylic acid (manufactured by Sigma-Aldrich Japan) and 0.30 g of 3-isopropylaniline were dissolved in 20 ml of methylene chloride, and 0.47 g of WSCI/HCl was added thereto while being cooled in ice. The mixture was stirred at room temperature for one hour, and refluxed for one hour to cause reaction. Then, the same reaction and posttreatment operation were performed as in Synthesis Example 1 to thereby obtain 0.54 g of pale yellow oily compound of 3'-isopropyl-2-methyl-4-trifluoromethyl-1,3-thiazole-5-carboxylic acid anilide.

$^1$H-NMR (CDCl$_3$) δppm; 7.78-7.00 (5H, m), 2.99-2.79 (1H, m), 2.75 (3H, s), 1.29 (3H, s), 1.22 (3H, s)

Synthesis Example 14

Comparative Compound 12

0.35 g of 2,5-dimethylpyrrole-3-carboxylic acid (manufactured by Sigma-Aldrich Japan) and 0.34 g of 3-isopropylaniline were dissolved in 20 ml of methylene chloride, and 0.53 g of WSCI/HCl was added thereto while being cooled in ice. The mixture was stirred at room temperature for one hour, and refluxed for one hour to cause reaction. Then, the same reaction and posttreatment operation were performed as in Synthesis Example 1 to thereby obtain 0.17 g of pale brown crystals of 3'-isopropyl-2,5-dimethylpyrrole-3-carboxylic acid anilide.

The melting point: 126 to 129° C., $^1$H-NMR (CDCl$_3$) δppm; 7.46-6.00 (6H, m), 2.97-2.74 (1H, m), 2.54 (3H, s), 2.22 (3H, s), 1.29 (3H, s), 1.21 (3H, s)

Synthesis Example 15

Comparative Compound 13

0.49 g of 1-methyl-3-trifluoromethylpyrazole-4-carboxylic acid (manufactured by Sigma-Aldrich Japan) and 0.34 g of 3-isopropylaniline were dissolved in 20 ml of methylene chloride, and 0.53 g of WSCI/HCl was added thereto while being cooled in ice. The mixture was stirred at room temperature for one hour, and refluxed for one hour to cause reaction. Then, the same reaction and posttreatment operation were performed as in Synthesis Example 1 to thereby obtain 0.34 g of colorless crystals of 3'-isopropyl-1-methyl-3-trifluoromethylpyrazole-4-carboxylic acid anilide.

The melting point: 131 to 134° C.

$^1$H-NMR (CDCl$_3$) δppm; 7.99-6.97 (6H, m), 3.97 (3H, s), 3.07-2.76 (1H, m), 1.30 (3H, s), 1.22 (3H, s)

Example 1

Each of 1% w/v dimethylsulfoxide solution of compound A, compound B and comparative compounds 1 to 13 was prepared. A predetermined amount of the solutions diluted with dimethylsulfoxide were fully mixed in the sterilized potato dextrose agar medium, and 15 ml of the resultant medium was poured into a petri dish 90 mm in diameter and allowed to stand at room temperature. As a control, the potato dextrose agar medium added with dimethylsulfoxide only was also prepared. After the medium was solidified, the mycelia was scooped with the medium from the colony of *Fomitopsis palustris* as being a typical wood-decaying fungi, which had been cultivated in advance, using a cork baller 5 mm in diameter; and inoculated in the center of the test medium. The fungi was cultivated in the petri dish at 25° C., and the diameter of the colony spread from the source of inoculum was measured on the seventh day. The growth inhibition ratio between the diameter of the test colony and that of the control was determined by the following formula as an indication of the degree of inhibition. The results are shown in Table 1. Compounds A and B apparently had greater effects on Fomitopsis palustris compared to the compounds which had been disclosed in the past.

Growth inhibition ratio (%)={(diameter of the control colony−diameter of the test colony)/diameter of the control colony}×100　　　[Formula 1]

TABLE 1

| Synthesis Example | Compound | Remark | Degree of inhibition on *Fomitopsis palustris* at 0.5 ppm |
|---|---|---|---|
| 1 | Compound A | | ○ |
| 2 | Compound B | | ○ |
| 3 | Comparative compound 1 | Compound disclosed by Japanese Patent No. 2825745 | ▲ |
| 4 | Comparative compound 2 | Compound disclosed by Japanese Patent No. 2825745 | ▲ |
| 5 | Comparative compound 3 | Compound disclosed by Japanese Patent No. 3083659 | x |
| 6 | Comparative compound 4 | Compound disclosed by JP-A-S53-9739, JP-A-S60-197603 & JP-B-S63-38966 | ▲ |
| 7 | Comparative compound 5 | Compound disclosed by JP-B-S63-38966 | ▲ |
| 8 | Comparative compound 6 | Compound disclosed by JP-B-S53-12973 | ▲ |
| 9 | Comparative compound 7 | | x |
| 10 | Comparative compound 8 | | ▲ |
| 11 | Comparative compound 9 | | x |
| 12 | Comparative compound 10 | | Δ |
| 13 | Comparative compound 11 | | ▲ |
| 14 | Comparative compound 12 | | x |
| 15 | Comparative compound 13 | | ▲ |

* Degree of inhibition:
○: inhibition ratio of 75% or more
Δ: inhibition ratio of 50 to 75%
▲: inhibition ratio of 25 to 50%
x: inhibition ratio of 25% or less

Example 2

Each of 1% w/v dimethylsulfoxide solution of compound A, compound B, cyproconazole (manufactured by Wako Pure Chemical Industries, Ltd.), epoxiconazole (manufactured by Wako Pure Chemical Industries, Ltd.) and tetraconazole (manufactured by Wako Pure Chemical Industries, Ltd.) was prepared. The solutions diluted with dimethylsulfoxide were fully mixed in the sterilized potate dextrose agar medium, and 15 ml of the resultant medium was poured into a petri dish 90 mm in diameter and allowed to stand at room temperature. As a control, the potate dextrose agar medium added with dimethylsulfoxide only was also prepared. After the medium was solidified, the mycelia was scooped with the medium from the colony of *Trametes versicolor* as being a typical wood-decaying fungi, which had been cultivated in advance, using a cork bailer 5 mm in diameter; and inoculated in the center of the test medium. The fungi was cultivated in the petri dish at 25° C., and the diameter of the colony spread from the source of inoculum was measured on the seventh day. The growth inhibition ratio by comparing the diameter of the test colony to that of the control was determined by the above-mentioned formula as an indication of the actual measured growth inhibition ratio. The results are shown in Table 2. The theoretical efficacy ratio of the mixture of the active ingredients (i.e. theoretical growth inhibition ratio) was determined using the following Colby's formula (R. S. Colby, Weeds 15, 20-22 (1967)) to thereby be compared with the actual-measured efficacy ratio (theoretical growth inhibition ratio). The results clearly show that compound A, compound B and a triazole-based fungicide have a synergetic effect.

Colby's formula: $E = x + y - x \cdot y/100$     [Formula 2]

E: theoretical efficacy ratio (theoretical growth inhibition ratio) represented by the ratio (%) to the control when the mixture of active compound B (concentration b) and C (concentration c) was used.

x: efficacy ratio (growth inhibition ratio) represented by the ratio (%) to the control when active compound B was used at a concentration of b.

y: efficacy ratio (growth inhibition ratio) represented by the ratio (%) to the control when active compound C was used at a concentration of c.

TABLE 2

| Fungus under test | Compounds under test | Concentration (ppm) | Actual measured growth inhibition ratio (%) | Theoretical growth inhibition ratio (%) |
|---|---|---|---|---|
| Trametes versicolor | Compound A | 0.2 | 49 | — |
| | Compound B | 0.2 | 44 | — |
| | cyproconazole | 0.2 | 33 | — |
| | Epoxiconazole | 0.2 | 24 | — |
| | Tetraconazole | 0.2 | 25 | — |
| | Compound A + cyproconazole | 0.2 + 0.2 | 100 | 66 |
| | Compound A + epoxiconazole | 0.2 + 0.2 | 98 | 61 |
| | Compound A + tetraconazole | 0.2 + 0.2 | 99 | 62 |
| | Compound B + cyproconazole | 0.2 + 0.2 | 99 | 62 |
| | Compound B + epoxyconazole | 0.2 + 0.2 | 98 | 57 |
| | Compound B + tetraconazole | 0.2 + 0.2 | 96 | 58 |

Example 3

A wood preservative containing 16 mass % of basic copper carbonate, 40 mass % of monoethanol amine and 5 mass % of benzoic acid using distilled water as a solvent. Compounds A and B which had been dissolved in a small amount of ethanol in advance and epoxyconazole were added to the wood preservative until the predetermined concentration is reached.

According to the protocol for the laboratory-scale decay assessment of the wood preservatives (PROTOCOLS FOR ASSESSMENT OF WOOD PRESERVATIVES, LABORATORY DECAY (THE AUSTRALASIAN WOOD PRESERVATION COMMITTEE)), the wood preservative was diluted with distilled water until the solution reaches a predetermined concentration and injected under pressure into the test sapwood of radiata pine (20×20×20 mm). The sapwood was air-dried and subjected to the resistance to climate operation according to the protocol. The test specimen provided on the flora of *Coniophora puteana*, which had been grown according to the protocol, was left to rot at 25° C. for 12 weeks, and the decrease rate due to the rotting in the mass of the sample specimen before and after testing was measured. The results are indicated by the average values calculated by using nine test specimens per one condition. The results are shown in Table 3. It was proved that a wood preservative having excellent preservation effect with a small chemical dosage can be obtained by using compound A and B, and by further blending a triazole-based fungicide at the same time, a wood preservative having excellent preservation effect with an extremely small amount dosage can be obtained.

TABLE 3

| Fungus under test | Preservative No. | Concentration of active ingredients in wood (*) | | | | Decrease rate in the mass due to the rotting (%) |
| --- | --- | --- | --- | --- | --- | --- |
| | | Copper (kg/m³) | Compound A (kg/m³) | Compound B (kg/m³) | Epoxiconazole (kg/m³) | |
| *Coniophora puteana* | No treatment | 0 | 0 | 0 | 0 | 45.1 |
| | 1 | 1.0 | 0 | 0 | 0 | 20.0 |
| | 2 | 1.0 | 0.005 | 0 | 0 | 2.5 |
| | 3 | 1.0 | 0.01 | 0 | 0 | 1.2 |
| | 4 | 1.0 | 0 | 0.005 | 0 | 2.9 |
| | 5 | 1.0 | 0 | 0.01 | 0 | 1.5 |
| | 6 | 1.0 | 0 | 0 | 0.05 | 17.5 |
| | 7 | 1.0 | 0 | 0 | 0.01 | 13.1 |
| | 8 | 1.0 | 0.005 | 0 | 0.005 | 0.1 |
| | 9 | 1.0 | 0 | 0.005 | 0.005 | 0.2 |

The invention claimed is:

1. A 5-methyl-2-trifluoromethylfuran-3-carboxylic acid anilide-based compound of the following formula:

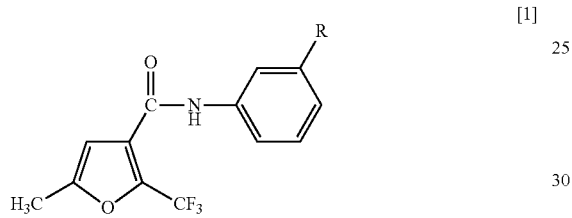

[1]

wherein, R represents an isopropyl group or an isopropoxy group.

2. A wood preservative containing 3'-isopropyl-5-methyl-2-trifluoromethylfuran-3-carboxylic acid anilide and/or 3'-isopropoxy-5-methyl-2-trifluoromethylfuran-3-carboxylic acid anilide according to claim 1 as an active ingredient.

3. The wood preservative according to claim 2 which further contains a triazole-based fungicide.

4. The wood preservative according to claim 3, wherein the triazole-based fungicide is one or more members selected from cyproconazole, epoxyconazole and tetraconazole.

5. The wood preservative according to claim 2, further containing at least one antibiotic compound.

6. The wood preservative according to claim 5, wherein the antibiotic compound is selected from copper compounds.

7. A wood preservative treatment method comprising applying the wood preservative according to claim 2 to wood.

* * * * *